United States Patent
Ceci et al.

(10) Patent No.: US 10,640,775 B2
(45) Date of Patent: May 5, 2020

(54) FUSION PROTEIN, NANOPARTICLE COMPOSED OF A PLURALITY OF MONOMERS OF SAID FUSION PROTEIN, AND USES THEREOF

(71) Applicant: Thena Biotech S.r.l., Latina (IT)

(72) Inventors: Pierpaolo Ceci, Rome (IT); Elisabetta Falvo, Rome (IT)

(73) Assignee: Thena Biotech S.r.l., Latina (IT)

( * ) Notice: Subject to any disclaimer, the term of this patent is extended or adjusted under 35 U.S.C. 154(b) by 103 days.

(21) Appl. No.: 15/515,875

(22) PCT Filed: Sep. 29, 2015

(86) PCT No.: PCT/IB2015/057448
§ 371 (c)(1),
(2) Date: Mar. 30, 2017

(87) PCT Pub. No.: WO2016/051340
PCT Pub. Date: Apr. 7, 2016

(65) Prior Publication Data
US 2017/0298364 A1    Oct. 19, 2017

(30) Foreign Application Priority Data
Sep. 30, 2014 (IT) .............................. TO2014A0779

(51) Int. Cl.
*C12N 15/62* (2006.01)
*C07K 14/47* (2006.01)
*A61K 47/64* (2017.01)
*A61K 39/00* (2006.01)
*A61K 39/395* (2006.01)
*B82Y 5/00* (2011.01)
*A61K 38/00* (2006.01)

(52) U.S. Cl.
CPC .......... *C12N 15/62* (2013.01); *A61K 39/0011* (2013.01); *A61K 39/39558* (2013.01); *A61K 47/64* (2017.08); *C07K 14/47* (2013.01); *A61K 38/00* (2013.01); *A61K 39/00* (2013.01); *B82Y 5/00* (2013.01); *C07K 2319/00* (2013.01); *C07K 2319/31* (2013.01); *C07K 2319/33* (2013.01); *C07K 2319/50* (2013.01)

(58) Field of Classification Search
None
See application file for complete search history.

(56) References Cited

PUBLICATIONS

International Search Report for PCT/IB2015/057448, five pages, dated Feb. 22, 2016.
Written Opinion of ISA for PCT/IB2015/057448, five pages, dated Feb. 22, 2016.
Falvo et al. "Antibody-drug conjugates: Targeting melanoma with cisplatin encapsulated in protein-cage nanoparticles based on human ferritin" *Nanoscale*, vol. 5, No. 24, pp. 12278-12285 (Jan. 2013).
Potrich et al. "Cytotoxic activity of a tumor protease-activated pore-forming toxin" *Bioconjugate Chemistry*, vol. 16, No. 9, pp. 369-376 (Mar. 2015).
Schoonen & Van Hest "Functionalization of protein-based nanocages for drug delivery applications" *Nanoscale*, vol. 6, No. 13, pp. 7124-7141 (Jul. 2014).
Vannucci et al. "Selective targeting of melanoma by PEG-masked protein-based multifunctional nanoparticles" *International Journal of Nanomedicine*, vol. 7, pp. 1489-1509 (Mar. 2012).
Vannucci et al. "Multifunctional protein-based nanoparticles for cancer theranosis" *Intracellular Delivery II*, Prokop et al. (eds.), pp. 231-253 (Jan. 2014).
Zhong & Chau "Antitumor activity of a membrane lytic peptide cyclized with a linker sensitive to membrane type 1-matrix metalloproteinase" *Molecular Cancer Therapeutics*, vol. 7, No. 9, pp. 2933-2940 (Sep. 2008).

*Primary Examiner* — Anand U Desai
(74) *Attorney, Agent, or Firm* — Sterne, Kessler, Goldstein & Fox P.L.L.C.

(57) ABSTRACT

A fusion protein based on the heavy chain of human ferritin is described, which includes at the N terminus of the protein at least one metalloproteinase cleavage sequence and a PAS polypeptide that acts as a masking polymer that increases the protein-drug stability, as well as a nanoparticle composed of multiple monomers of said fusion protein, a nucleic acid encoding for said fusion protein, and diagnostic and therapeutic applications thereof.

13 Claims, 13 Drawing Sheets

Specification includes a Sequence Listing.

| Protein | Protein recovery (%) | Number of encapsulated doxorubicin molecules |
|---|---|---|
| HFt-MMP-PAS75 | 96±4 | 94±4 |
| HFt-MMP-PAS40 | 95±3 | 90±3 |
| Human native HFt | 40±4 | 29±3 |
| Human native HFt [1] | 53.33 | 11 |
| Human native HFt [2] | n.d. | 33 |
| Equine native HFt [3] | 48±9 | 23±3 |

1. Zhen Z et al., ACS Nano. 2013 Jun 25;7(6):4830-7
2. Liang M et al., Proc Natl Acad Sci U S A. 2014 Oct 14;111(41):14900-5
3. Kilic MA et al., J Biomed Nanotechnol. 2012 Jun;8(3):508-14

Fig. 8

SEQUENCE LISTING

<160> NUMBER OF SEQ ID NOS: 10

<210> SEQ ID NO 1
<211> LENGTH: 183
<212> TYPE: PRT
<213> ORGANISM: Homo sapiens

<400> SEQUENCE: 1

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
                20                  25                  30

Tyr Val Tyr Leu Ser Met Ser Tyr Tyr Phe Asp Arg Asp Asp Val Ala
            35                  40                  45

Leu Lys Asn Phe Ala Lys Tyr Phe Leu His Gln Ser His Glu Glu Arg
        50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Asn
            100                 105                 110

Gln Ser Leu Leu Glu Leu His Lys Leu Ala Thr Asp Lys Asn Asp Pro
        115                 120                 125

His Leu Cys Asp Phe Ile Glu Thr His Tyr Leu Asn Glu Gln Val Lys
        130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser
                180

<210> SEQ ID NO 2
<211> LENGTH: 183
<212> TYPE: PRT
<213> ORGANISM: Artificial Sequence
<220> FEATURE:
<223> OTHER INFORMATION: Variant heavy chain human ferritin (vHFt)

<400> SEQUENCE: 2

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
                20                  25                  30

Tyr Val Tyr Leu Ser Met Ser Tyr Tyr Phe Asp Arg Asp Asp Val Ala
            35                  40                  45

Leu Lys Asn Phe Ala Lys Tyr Phe Leu His Gln Ser His Glu Lys Arg
        50                  55                  60

Glu Gly Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Asn
            100                 105                 110

Gln Ser Leu Leu Glu Leu His Lys Leu Ala Thr Asp Lys Asn Asp Pro
        115                 120                 125

His Leu Cys Asp Phe Ile Glu Thr His Tyr Leu Asn Glu Gln Val Lys
        130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser
            180

<210> SEQ ID NO 3
<211> LENGTH: 8
<212> TYPE: PRT
<213> ORGANISM: Artificial Sequence
<220> FEATURE:
<223> OTHER INFORMATION: Peptide mimicking an MMP cleavage site

<400> SEQUENCE: 3

Gly Pro Leu Gly Ile Ala Gly Gln
1               5

<210> SEQ ID NO 4
<211> LENGTH: 8
<212> TYPE: PRT
<213> ORGANISM: Artificial Sequence
<220> FEATURE:
<223> OTHER INFORMATION: Peptide mimicking an MMP cleavage site

<400> SEQUENCE: 4

Gly Pro Gln Gly Ile Trp Gly Gln
1               5

<210> SEQ ID NO 5
<211> LENGTH: 6
<212> TYPE: PRT
<213> ORGANISM: Artificial Sequence
<220> FEATURE:
<223> OTHER INFORMATION: Peptide mimicking an MMP cleavage site

<400> SEQUENCE: 5

Pro Leu Gly Leu Ala Gly
1               5

<210> SEQ ID NO 6
<211> LENGTH: 6
<212> TYPE: PRT
<213> ORGANISM: Artificial Sequence
<220> FEATURE:
<223> OTHER INFORMATION: Peptide mimicking an MMP cleavage site

<400> SEQUENCE: 6

Pro Val Gly Leu Ile Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Peptide mimicking an MMP cleavage site

<400> SEQUENCE: 7

Cys Gly Leu Asp Asp
1               5

<210> SEQ ID NO 8
<211> LENGTH: 16
<212> TYPE: PRT
<213> ORGANISM: Artificial Sequence
<220> FEATURE:
<223> OTHER INFORMATION: Peptide with repeated MMP cleavage sites

<400> SEQUENCE: 8

```
Gly Pro Leu Gly Ile Ala Gly Gln Gly Pro Leu Gly Ile Ala Gly Gln
1               5                   10                  15
```

<210> SEQ ID NO 9
<211> LENGTH: 40
<212> TYPE: PRT
<213> ORGANISM: Artificial Sequence
<220> FEATURE:
<223> OTHER INFORMATION: PAS polypeptide

<400> SEQUENCE: 9

```
Ala Ser Pro Ala Ala Pro Ala Pro Ala Ser Pro Ala Ala Pro Ala Pro
1               5                   10                  15

Ser Ala Pro Ala Ala Ser Pro Ala Ala Pro Ala Pro Ala Ser Pro Ala
                20                  25                  30

Ala Pro Ala Pro Ser Ala Pro Ala
            35                  40
```

<210> SEQ ID NO 10
<211> LENGTH: 75
<212> TYPE: PRT
<213> ORGANISM: Artificial Sequence
<220> FEATURE:
<223> OTHER INFORMATION: PAS polypeptide

<400> SEQUENCE: 10

```
Ala Ser Pro Ala Ala Pro Ala Pro Ala Ser Pro Ala Ala Pro Ala Pro
1               5                   10                  15

Ser Ala Pro Ala Ala Ser Pro Ala Ala Pro Ala Pro Ala Ser Pro Ala
                20                  25                  30

Ala Pro Ala Pro Ser Ala Pro Ala Ala Ser Pro Ala Ala Pro Ala Pro
            35                  40                  45

Ala Ser Pro Ala Ala Pro Ala Pro Ser Ala Pro Ala Ala Ser Pro Ala
        50                  55                  60

Ala Pro Ala Pro Ala Ser Pro Ala Ala Pro Ala
65                  70                  75
```

FUSION PROTEIN, NANOPARTICLE COMPOSED OF A PLURALITY OF MONOMERS OF SAID FUSION PROTEIN, AND USES THEREOF

This application is the U.S. national phase of International Application No. PCT/IB2015/057448, filed 29 Sep. 2015, which designated the U.S. and claims priority to Patent Application No. IT TO2014A000779, filed 30 Sep. 2014; the entire contents of each of which are hereby incorporated by reference.

The present invention relates to a fusion protein, nanoparticles composed of a plurality of monomers of said fusion protein, nucleic acids encoding said fusion protein, and diagnostic and therapeutic applications thereof.

The selective release of therapeutic agents at diseased areas represents one of the most important challenges for improving the current therapies. In this context, the use of nanoparticles as carriers (nanovectors) of therapeutic agents potentially allows for both circumventing the biological barriers that may be present between the administration site and the final target and, more specifically, accumulating the drug in a selective way at the diseased area rather than in normal tissues. As a fundamental prerequisite, the nanovector must be able to bind large amounts of the drug in an effective way.

Among the known carriers for targeted drug release, nanoparticles based on ferritins (Fts) are becoming increasingly interesting thanks to their extraordinary characteristics of biocompatibility, ability of crossing biological barriers, functionalization versatility, and capability of binding certain types of drugs (Vannucci, L., Falvo, E., Ceci, P. Multifunctional Protein-Based Nanoparticles for Cancer Theranosis. 2014, A. Prokop et al. (eds.), Intracellular Delivery II, Fundamental Biomedical Technologies 7). Fts are highly symmetrical multimeric protein structures consisting of 24 subunits that assemble into a molecular structure with an essentially spherical shell, which encloses a cavity that is physiologically used for storing iron. The outer diameter and the inner diameter are 12 and 8 nm, respectively. Such a shell-shaped molecular structure will be hereinafter designated as "nanoparticle" or "HFt nanoparticle".

Nanoparticles based on the heavy chain of human ferritin (HFt) show a number of advantages compared to other drug release systems, especially in connection with in vivo human applications. In fact, the HFt molecules are designed to cross the biological barriers (20 nm minor diameter) and are present both within cells and in blood under physiological conditions, although at low concentrations (approximately 20 μg/L).

Being natural elements, they are less likely to evoke a strong non-self (extraneous) antibody and/or T cell immune response.

Furthermore, HFt is one of the few natural nanoparticles that is capable by itself of binding tumour cells in an effective and selective way. In fact, by using one of the most attractive molecules for targeted cancer therapy, transferrin receptor 1 (TfR1), it has been shown that HFt is internalized. TfR1 is indeed up-regulated at the surface of many types of cancer (up to 100 times higher than in normal cells) and is efficiently internalized. In more than 474 clinical tissue samples, HFt, but not the light chain of human ferritin (LFt), was proven to be internalized by TfR1 and to specifically recognize many types of tumours (i.e. liver, lung, pancreas, colon, cervix, ovary, prostate, breast, sarcoma, and thymus cancers) compared to non-tumour tissues, with 98% sensitivity and 95% specificity (Fan K, Cao C, Pan Y, Lu D, Yang D, Feng J, et al. Magnetoferritin nanoparticles for targeting and visualizing tumour tissues. Nat Nanotechnol. 2012; 7:459-64).

However, native HFt exhibits a few disadvantages. Firstly, the yields with which it is capable of binding certain types of drugs, such as for example doxorubicin (one of the anti-neoplastic drugs with a broad anti-tumour spectrum) are low, and this may restrict their possible use and clinical development. Secondly, native HFt has a very short plasma half-life, approximately 2-3 hours, when injected through the systemic route. Lastly, its natural ferroxidase activity might inhibit the development and maturation of human osteoblasts, and bring about a decreased mineralization, osteopenia and osteoporosis (Zarjou A, Jeney V, Arosio P, Poli M, Zavaczki E, Balla G, Balla J. Ferritin ferroxidase activity: a potent inhibitor of osteogenesis. J Bone Miner Res. 2010, 25:164-72). For this reason, it is advisable to use an HFt variant lacking the ferroxidase activity, obtained by site-specific mutation (hereinafter designated as vHFt), which gives no inhibition.

In order to simultaneously solve all the disadvantages listed above with regard to native HFt, the present inventors decided to genetically modify the heavy chain of human ferritin (HFt) by acting directly on the outer surface of the protein. In so doing, the ability to encapsulate the drug doxorubicin within the protein cavity improved drastically and surprisingly, and the plasma half-life was extended without affecting the protein's ability of recognizing tumour cells.

This and other objects are accomplished through the fusion protein as defined in appended claim 1. The other independent claims and the dependent claims relate to further aspects and specific embodiments of the invention, which form an integral part of the specification.

BRIEF DESCRIPTION OF THE DRAWINGS

Further features and advantages of the invention will appear from the following detailed description, which is provided for illustrative purposes only and not by way of limitation, with reference to the appended drawings, wherein:

FIG. 8 shows the ability to encapsulate doxorubicin by two of the established constructs (HFt-MMP-PAS40 and HFt-MMP-PAS75) compared to that of the native HFt protein and with other data from the literature. The relative yields are indicated in terms of % protein recovery and number of doxorubicin molecules encapsulated. It can be seen that the constructs subject matter of this patent surprisingly and unexpectedly have acquired an improved ability of encapsulating the drug doxorubicin by at least a factor of 6 compared to native HFt.

Figure 1:
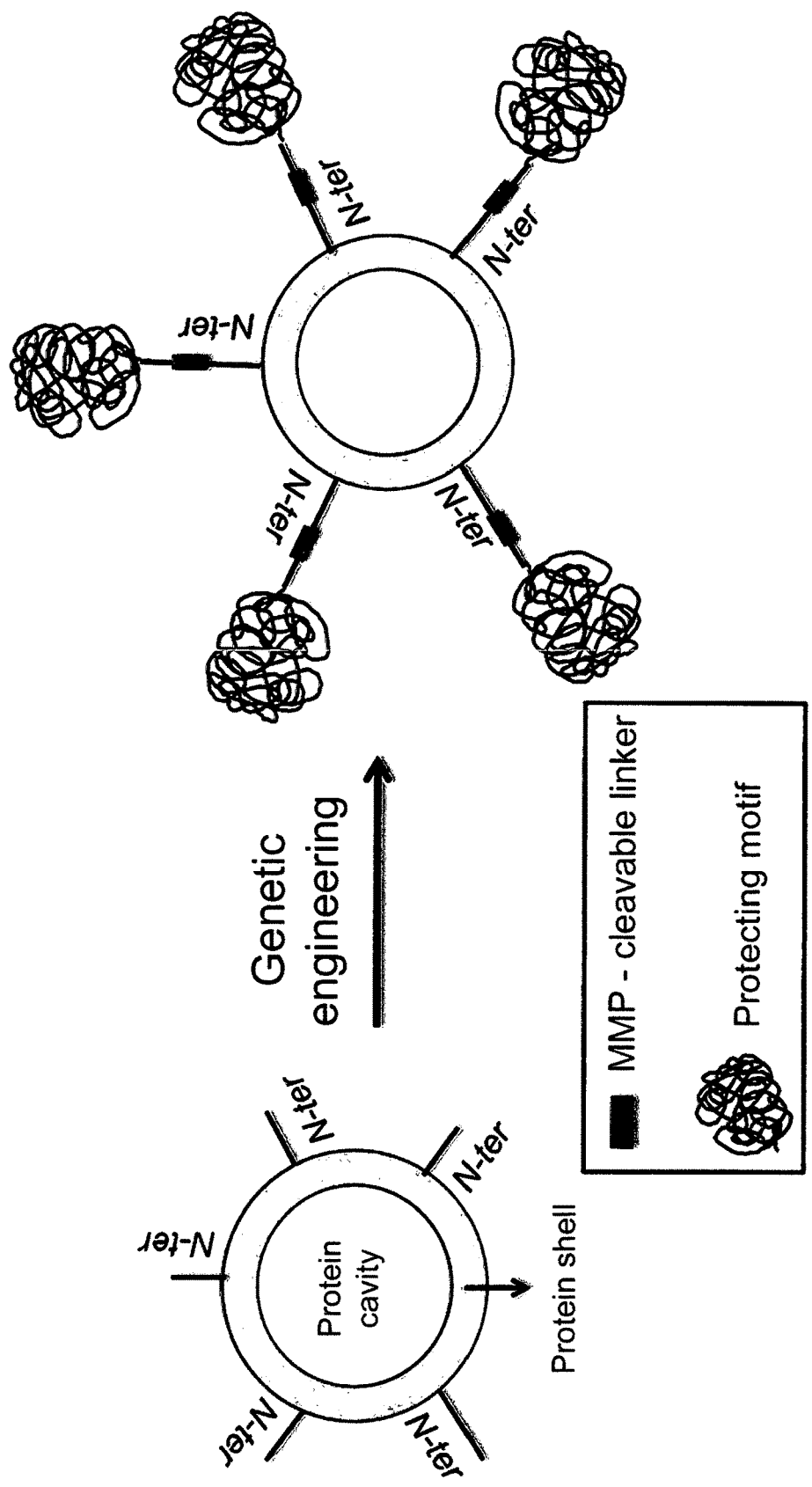
FIG. 1 is a schematic representation of the manufacture of HFt nanoparticles, wherein the N terminus of each of the 24 monomers is genetically bound to cleavable peptide sequences and to sequences essentially consisting of proline, alanine and serine (PAS). For the sake of clarity, only 5 of the 24 N terminal ends present are shown.

The fusion protein which is the subject matter of the present invention comprises at least three domains.

The first domain comprises the amino acid sequence of the heavy chain of human ferritin. Such an amino acid sequence is the native sequence or is a variant of the native sequence having at least 90% sequence identity. Since the heavy chain of human ferritin has a length of 183 amino acids (SEQ ID NO: 1), a variant having at least 90% sequence identity contains up to 19 amino acid substitutions compared to the native sequence. This definition includes, inter alia, the amino acid sequence SEQ ID NO: 2 of the above-mentioned vHFt variant lacking the ferroxidase activity, which represents an alternative variant. The amino acid sequence of vHFt is characterized by two amino acid substitutions: Lysine instead of Glutamate 62 and Glycine instead of Histidine 65.

The second domain of the fusion protein of the invention comprises the amino acid sequence of at least one matrix metalloproteinase (MMP) cleavage site, particularly MMP-2, MMP-3, MMP-7 or MMP-9. As a non-limiting example, hereinafter a few peptides are listed, which simulate the cleavage sequence of the collagen chain and are cleaved in a particularly effective way by MMP-2 and MMP-9:

```
                                        (SEQ ID NO: 3)
         Gly-Pro-Leu-Gly-Ile-Ala-Gly-Gln (SEQ ID NO: 4)
         Gly-Pro-Gln-Gly-Ile-Trp-Gly-Gln (SEQ ID NO: 5)
         Pro-Leu-Gly-Leu-Ala-Gly (SEQ ID NO: 6)
         Pro-Val-Gly-Leu-Ile-Gly (SEQ ID NO: 7)
         Cys-Gly-Leu-Asp-Asp
```

The amino acid sequences that contain the cleavage site for the intended enzyme can also be constructed in such a way that the cleavage site is repeated several times, such as for instance in the sequence as shown below:

```
                                        (SEQ ID NO: 8)
Gly-Pro-Leu-Gly-Ile-Ala-Gly-Gln-Gly-Pro-Leu-Gly-
Ile-Ala-Gly-Gln.
```

All the previously mentioned amino acid sequences are representative, but not limitative, examples of the manufacture of the fusion proteins and the nanoparticles according to the present invention.

The third domain of the fusion protein of the invention, linked to the N terminus, consists of the amino acid sequence of a polypeptide which is rich in proline, serine and alanine (referred to as "PAS" for the sake of brevity), having the aim of increasing the stability of the protein during the drug encapsulating process, preferably for the drug doxorubicin, and of increasing the stability of the protein-drug complex. The presence of PAS is also capable of masking the protein surface and thus of extending its plasma half-life.

The polypeptide PAS consists mainly of amino acid sequences rich in Pro, Ala and Ser, which form an unstructured polymer, the length of which is preferably lower than 80 amino acid residues, more preferably comprised between 20 and 80 amino acid residues, still more preferably comprised between 40 and 75 amino acid residues. In a preferred embodiment, the proline residues of the aforesaid polypeptide PAS amount to 10-40% of the total amino acid residues of the polypeptide PAS.

Examples of PAS polypeptides particularly suitable to be used within the scope of the present invention, and therefore preferred, are PAS polypeptides of 40 or 75 amino acid residues, such as for example the following:

(SEQ ID NO 9)
ASPAAPAPASPAAPAPSAPAASPAAPAPASPAAPAPSAPA (SEQ ID NO 10)
ASPAAPAPASPAAPAPSAPAASPAAPAPASPAAPAPSAPAASPAAPAPA
SPAAPAPSAPAASPAAPAPASPAAPA

The stabilizing and masking PAS polypeptide is added to the surface of HFt through a short peptide sequence that, as previously mentioned above, contains one or more metalloproteinase cleavage sites, so as to provide the fusion protein of the invention with a displaceable masking. In fact, PAS polypeptide can be selectively removed at the target tissues by extracellular matrix metalloproteinases (MMPs). In particular, MMP-2 and MMP-9 were shown to be key metalloproteinases that are overexpressed in the tumour microenvironment and are involved in angiogenesis, invasion, and tumour metastasis.

The use of PAS polypeptides on the multimeric surface of ferritin within the scope of the present invention offers several advantages over the prior art. In order to encapsulate a drug or small molecules within the protein cavity of ferritin, to date the most obvious actions were undertaken, that is directly modifying the drug or the protein's inner cavity itself. In this way, the interaction between the drug (or small molecule) and the binding sites in the inner cavity of ferritin is favoured. For instance, doxorubicin was pre-complexed with copper (II) to increase the encapsulation yield (Zhen Z et al., ACS Nano. 2013 Jun. 25; 7(6):4830-7). Gold nanoparticles were encapsulated by genetically modifying the inner cavity of ferritin with a gold-binding peptide (Zheng B et al. Nanotechnology. 2010 Jan. 29; 21(4): 045305). However, the present inventors have decided to act directly on the outer protein surface by using inert PAS polymers in order to stabilize the protein during the sudden change of pH which is generally used for dissociating (pH 2.0) and re-associating (pH 7.5) HFt in the presence of the drug. The presence of the PAS polymer might also limit the non-specific binding of the drug on the surface itself.

Further, the presence of PAS may also represent a method of extending the plasma half-life of a protein, as the XL-protein Gmbh company has recently proposed for a number of proteins. In fact, the technology designated as "PASylation" is capable of extending the plasma half-life of bio-pharmaceuticals by using a naturally unstructured amino acid chain as a biological alternative to PEG (Schlapschy M, Binder U, Börger C, Theobald I, Wachinger K, Kisling S, Haller D, Skerra A. PASylation: a biological alternative to PEGylation for extending the plasma half-life of pharmaceutically active proteins. Protein Eng Des Sel. 2013, 26:489-501). Using this technique, a biologically active protein is genetically fused with a polypeptide sequence comprising several hundreds of residues of the small amino acids proline, serine and alanine (PAS). Generally, a PAS sequence consists of 100-3000 residues (preferably 400-600 residues) fused to a biologically active protein. The biologically active proteins mentioned in patent WO 2008/155134 fall within the following categories: binding proteins, antibody fragments, cytokines, growth factors, enzymes, hormones. The heavy chain of human ferritin is not mentioned and, especially in the vHFt form, does not belong to the categories listed. According to the tests carried out by the present inventors, which will be described in further detail hereinafter, for the heavy chain of human (native or variant) ferritin, the PAS sequence can be much shorter than described in WO 2008/155134, for example lower than 80 amino acid residues. In other words, by exploiting the particular ability of HFt to form a nanoparticle consisting of 24 monomers, much shorter PAS sequences prove to be effective and efficient in extending the plasma half-life of HFt in vivo. The selection of the length of the masking PAS polypeptide is a critical step in the development of an HFt provided with the desired characteristics. In fact, on the one hand the in vivo half-life must be sufficiently long as to allow HFt to accumulate at the desired site. On the other hand, HFt must be able to free itself from the masking polymer in environments rich in metalloproteinases (MMP). If the PAS sequence is too short, the construct might be cleared too quickly from the organism. If the PAS sequence is too long, it might hinder the crossing through biological barriers that separate it from the target tissue and cells (i.e. blood vessels, tight junctions, tumour stroma, etc.) and/or mask the MMP cleavage site or sites.

Furthermore, the achievement of a final protein product that is overexpressed, fully soluble, and that folds and assembles properly is not obvious beforehand when the N terminus of the protein is modified, as in the case of the fusion protein of the present invention. Indeed, it is well known that the N-terminal modification of a protein can impair the expression, solubility and/or proper folding and assembly thereof.

All of these results, particularly the improvement of the encapsulation yields of the drug doxorubicin, have been surprisingly and unexpectedly achieved by the present inventors, who constructed nanoparticles based on the heavy chain of human ferritin (HFt), in the native form or in a variant form (preferably vHFt), by using both the gene fusion technology and the production technology of recombinant proteins. In particular, as will be described in detail in the section related to the examples, genetic constructs were made, which, in one single nucleic acid sequence (for instance DNA), encode for the three sequences set forth in FIG. 1: i) HFt (or vHFt); ii) short peptide sequences (MMP) cleavable by MMP-2/9; iii) unstructured polypeptide sequences rich in Pro, Ser and Ala (PAS) preferably with a length comprised between 20 and 80 residues. Sequences ii) and iii) are bound to the N terminus of HFt for a reversible masking thereof.

In some embodiments, the fusion protein HFt of the invention comprises a first and/or second linker amino acid sequence(s) respectively linking the first domain to the second domain and/or the second domain to the third domain. The first and/or second amino acid sequences can be the same or different from each other.

Figure 2:
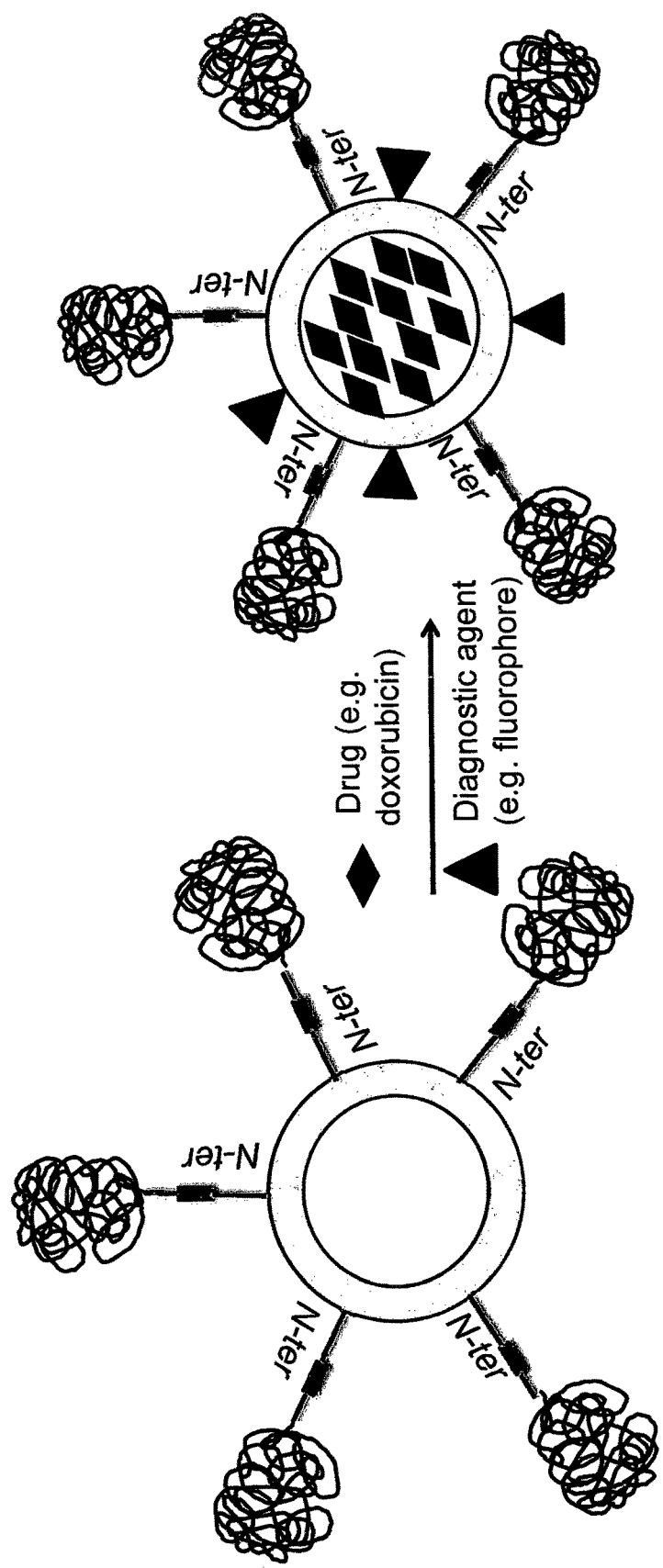
FIG. 2 is a schematic representation of the manufacture of HFt nanoparticles that carry therapeutic and/or diagnostic molecules. These may be loaded in the inner cavity or bound to the outer surface of the protein.

As already stated above, the HFt fusion proteins obtained by the present inventors spontaneously form HFt nanoparticles capable of carrying therapeutic (chemical compounds, monoclonal antibodies, peptides, etc.) and/or diagnostic molecules (FIG. 2). In a preferred embodiment, at least 5 therapeutic and/or diagnostic molecules are encapsulated in the inner cavity of the HFt nanoparticle or are covalently bound to the surface of the HFt nanoparticle. The amount of bound drug and the stability of the protein-drug complex itself are considerably increased compared to the unmodified protein thanks to the presence of the PAS polypeptides. As used herein, the term "stability of the protein-drug complex" refers to the ability of the HFt fusion protein to retain the drug in the cavity and not to release it over time during the storage life of the complex. Release of the drug from the HFt protein before its final use can cause undesirable effects, such as precipitation, clustering, and loss of the final product.

Figure 3:
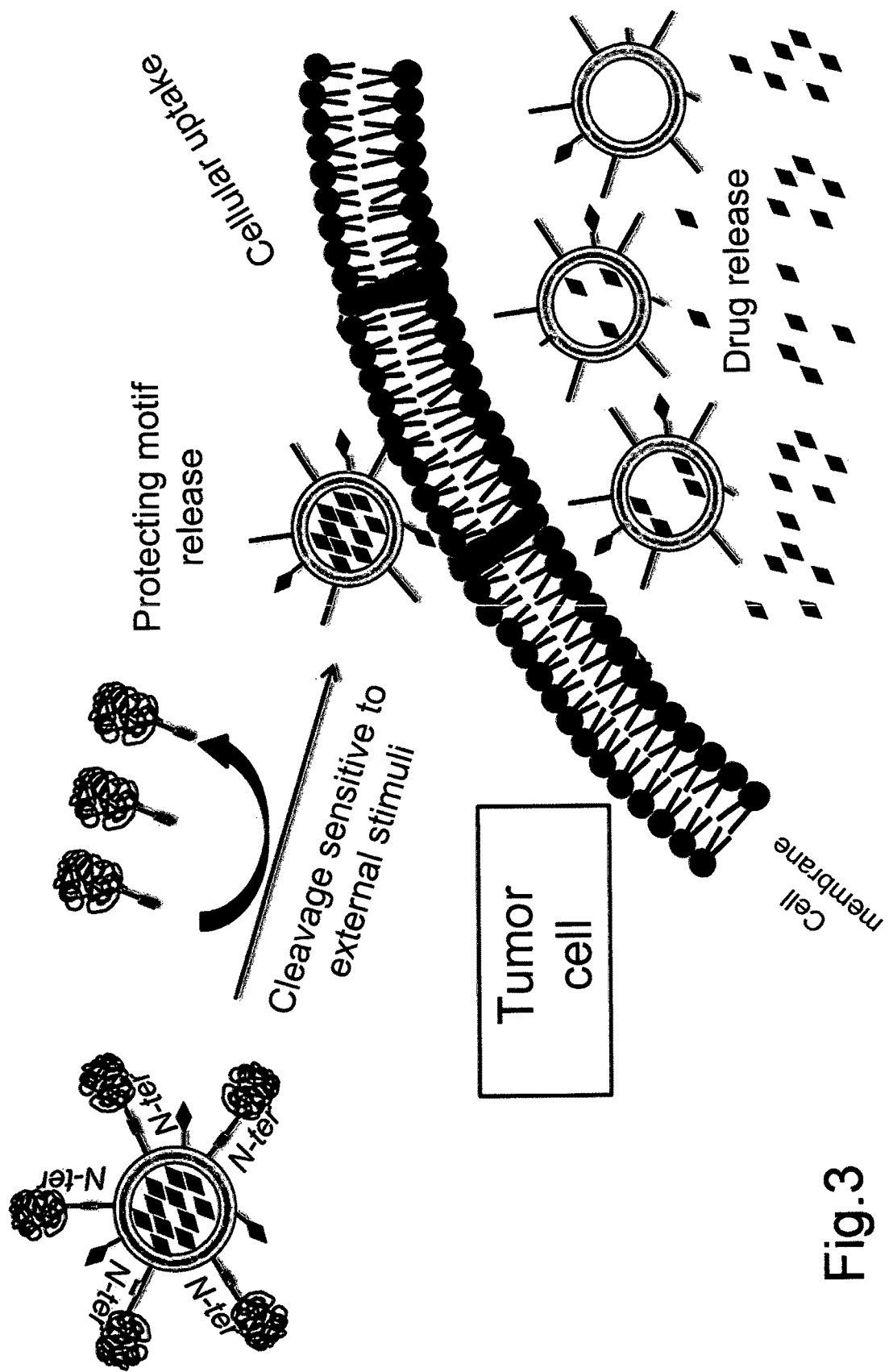
FIG. 3 is an overall diagram that describes the mode of action of the HFt nanoparticles on tumour cells.

The HFt nanoparticles of the present invention, which act as targeted binding and releasing systems for drugs or diagnostic agents, will temporarily be inactive in the circulation and in tissues that do not express MMPs or that express them inadequately, and will subsequently be activated when they reach target tissues rich in MMPs (MMP-2/9) wherein their load can be released (FIG. 3). A therapeutic molecule is for example a pharmaceutical active ingredient. As used herein, the expression "pharmaceutical active ingredient" or more simply "active ingredient" refers to any pharmaceutically active molecule (chemical compound, monoclonal antibody, peptide, etc.), for instance a molecule that can be used for cancer treatment. Preferred active ingredients for use in the present invention are for example, without limitation, doxorubicin, paclitaxel, gemcitabine and platinum-based active ingredients. A precursor of the active ingredients listed above may also be used.

A diagnostic molecule is for example an imaging agent. As used herein, the term "imaging agent" relates to a molecule that allows for the visualization of organs, tissues, or body systems. Exemplary imaging agents include paramagnetic agents, optical probes, and radionuclides. The term "optical probe" refers to a fluorescent compound that can be detected by excitation at a first wavelength and reading at a second wavelength. Exemplary optical probes include fluorescein isothiocyanate and 5-(and 6)-carboxytetramethylrhodamine, succinimidyl ester.

In diagnostic and therapeutic applications, the HFt nanoparticles of the present invention, which act as targeted carrier systems, can be administered to a subject or patient through any suitable administration route, for instance orally, parenterally, intravenously, intraperitoneally, intramuscularly, as a suppository, intralesionally, intranasally or subcutaneously, intrathecally, intralymphatically, through inhalation of microdroplets, or by implant of a slow-release device, for instance an osmotic pump. As used herein, the term "subject" relates to animals, such as mammals, including human beings, cows, sheep, goats, horses, dogs, cats, rabbits, rats, mice and the like.

As used herein, the term "treating" or "treatment" refers to evidence of success or improvement in the treatment of a certain disease, lesion, condition or symptom, or, in certain circumstances, the prevention of the onset of a symptom or condition.

In therapeutic applications, the HFt nanoparticles of the invention are used for the administration of a therapeutically effective dose of a pharmaceutical active ingredient. "Therapeutically effective dose" is intended to mean a dose that produces the therapeutic effect for which it is administered. The exact dose will depend on a number of factors, including to the aim of the treatment, the subject, the disease to be treated, etc., and can easily be determined by a person of ordinary skill in the art by using per se known methodologies (see, for example, Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

The HFt nanoparticles of the invention may be used for treating any disease that requires the administration of a pharmaceutical ingredient, for instance by sequestering the active ingredient within the cavity of the nanoparticle or by covalently binding it to the nanoparticle surface. The nanoparticles can also be used for diagnosis, more particularly for the imaging of diseases, by sequestering an imaging agent within the cavity of the nanoparticle or by covalently binding it to the nanoparticle surface.

The HFt nanoparticle of the present invention can be administered to a subject for the treatment of any disease, preferably a hyperproliferative disease, including cancer, for example: carcinomas, gliomas, mesotheliomas, melanomas, sarcomas, lymphomas, leukaemias, adenocarcinomas, breast cancer, ovary cancer, cervical cancer, glioblastoma, leukaemia, lymphoma, prostate cancer, Burkitt's lymphoma, head and neck cancer, colon cancer, colorectal cancer, non-small cell lung cancer, small cell lung cancer, oesophagus cancer, stomach cancer, pancreatic cancer, hepatobiliary cancer, bladder cancer, small intestine cancer, rectal cancer, kidney cancer, gall bladder cancer, penile cancer, urethra cancer, testicular cancer, cervix cancer, vaginal cancer, uterine cancer, thyroid cancer, parathyroid cancer, adrenal cancer, endocrine pancreatic cancer, carcinoid tumour, bone cancer, skin cancer, retinoblastomas, multiple mielomas, Hodgkin lymphoma, non-Hodgkin lymphoma (see CANCER: PRINCIPLES AND PRACTICE (DeVita, V. T. et al. 2008 Edition) for other types of cancer).

The following examples are provided for illustrative purposes and not as a limitation of the scope of the invention as defined in the appended claims.

EXAMPLES

Example 1

Construction of Expression Vectors for HFt-MMP-PAS40 and HFt-MMP-PAS75 Fusion Proteins As the first step to design a HFt-MMP-PAS (or vHFt-MMP-PAS) construct, several molecular models were constructed based on the three-dimensional structure of HFt, which had been determined experimentally by X ray crystallography and is available at the Protein Data Bank (PDB) under the code 3AJO. In order to modify this structure computationally, the InsightII molecular modelling software (Accelrys Inc.) was used.

i) In order to construct a model of the HFt variant described in Vannucci et al. (2012), which has a suitable hydrodynamic volume, a polymer containing 110 PEG units, which was bound to the —SH groups displayed on the surface of HFt, was used. The PEG polymers were modelled into a tightly packed conformation on the protein surface, to reflect the hydrodynamic volume that had been measured experimentally for the sustained-circulation PEGylated HFt (PEG 5 kDa) (see Vannucci et al., 2012).

ii) In order to construct a model of the new HFt, the selected MMP cleavage sequence (SEQ ID NO: 5) was bound to the exposed N terminus of each HFt subunit (SEQ ID NO: 1) and a number of PAS polymers of different lengths were constructed. These PAS polymers were attached to the MMP cleavage sequence through three glycine residues and their volume was compared to that of the PEGylated HFt. Initially, two PAS lengths were selected as they reflected two different scenarios, that is an extended conformation (PAS40) and a more packed conformation (PAS75), taking into account that, owing to the presence of the peptide bonds and proline residues, the PAS polymers have significantly decreased degrees of freedom compared to a highly flexible PEG.

The HFt-MMP-PAS40 gene was achieved by combining three different sequences into one single sequence: HFt (SEQ ID NO: 1), MMP (SEQ ID NO: 5) and PAS (SEQ ID NO: 9). A linker consisting of three glycine residues was inserted between HFt and MMP and between MMP and PAS.

The HFt-MMP-PAS75 gene was achieved by combining three different sequences into one single sequence: HFt (SEQ ID NO: 1), MMP (SEQ ID NO: 5) and PAS (SEQ ID NO: 10). A linker consisting of three glycine residues was inserted between HFt and MMP and between MMP and PAS.

The pET-11a expression vector containing the HFt-MMP-PAS40 gene or the HFt-MMP-PAS75 gene was synthesized by using GENEART AG (Germania). Gene synthesis was carried out taking into consideration the codon optimization for high levels of expression in *Escherichia coli*.

Example 2

Bacterial Expression and Purification of HFt-MMP-PAS40 and HFt-MMP-PAS75 Fusion Proteins The pET-11a expression vectors containing HFt-MMP-PAS40 or HFt-MMP-PAS75 from Example 1 were inserted in *E. coli* BL21 (DE3) and sequenced by the dideoxy sequencing method to confirm the presence of the correct gene. *E. coli* BL21 (DE3) cells containing the recombinant plasmid were cultured up to an $OD_{600}$ of 0.6 at 37° C. in 1 L of Terrific Broth (TB) liquid medium containing ampicillin (23.6 g/L yeast extract, 11.8 g/L Tryptone, 9.4 g/L $K_2HPO_4$, 2.2 g/L $KH_2PO_4$). Gene expression was induced by adding 0.5 mM isopropyl thio-β-D-galactoside (IPTG) and the culture was further incubated for 3 hours. The cells were collected by centrifugation (15000 rpm for 20 minutes), suspended in 50 mM Tris-HCl (pH 7.5), 0.5 mM dithiothreitol, 1 mM EDTA, and 300 mM NaCl, and disrupted by sonication. The lysate was centrifuged at 15000 rpm for 40 minutes and the supernatant containing the soluble fraction was treated for 30 minutes at 37° C. with 0.1 mg/mL DNase enriched with 5 mM $MgCl_2$, heated to 75° C. for 10 minutes, cooled on ice, and then centrifuged to remove the denatured proteins. The recovered supernatant was precipitated by using a concentration of 65% saturated (w/v) ammonium sulphate. The pellet was resuspended and dialysed overnight against 30 mM Tris-HCl, pH 7.5, 0.25 M NaCl, and then loaded on a Superdex 200 hiload 26/600 column (GE Healthcare) previously equilibrated with phosphate-buffered saline (PBS). The fractions were pooled, concentrated, sterile filtered and stored at 4° C. The purity of all the preparations was assessed by using Coomassie blue staining of a 15% PAGE gel run in the presence of SDS. The protein concentration was determined spectrophotometrically at 280 nm using a molar extinction coefficient obtained with the ProtParam software (www.expasy.org).

Figure 4:
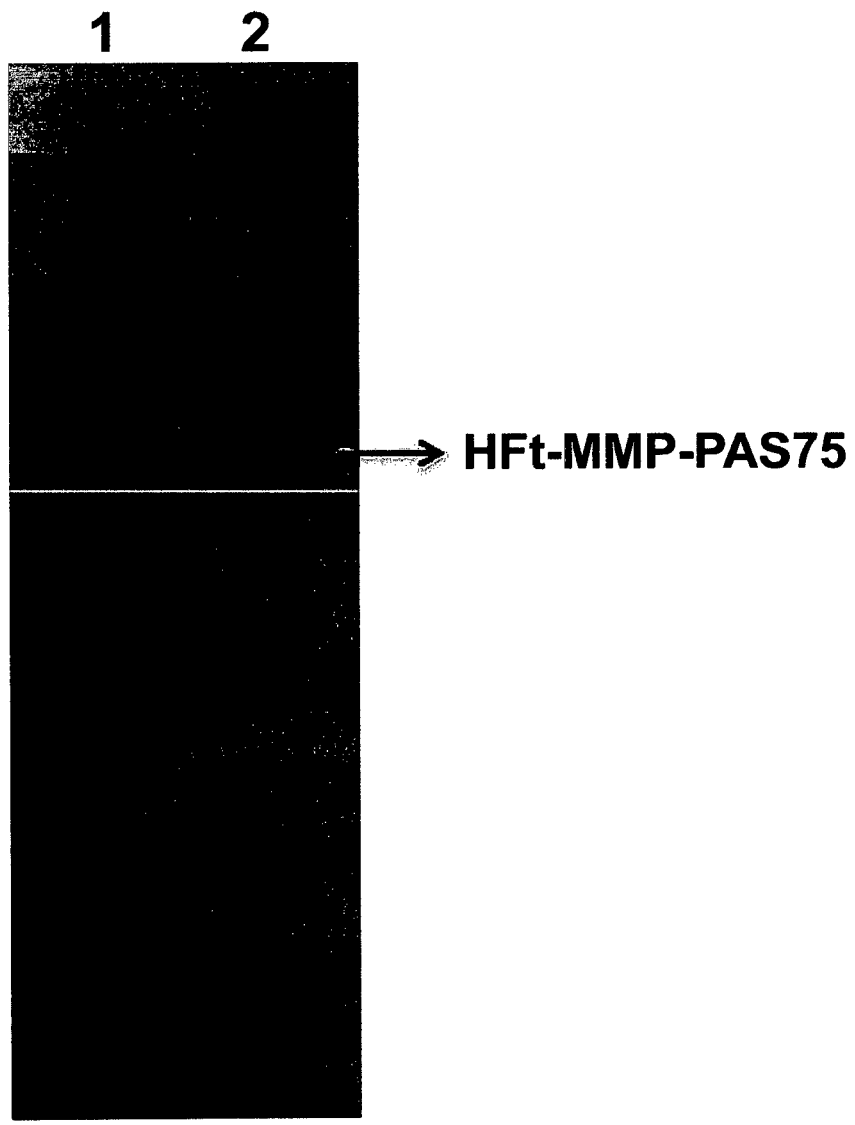
FIG. 4 shows the protein expression profile of one of the established constructs, HFt-MMP-PAS75 (PAS length: 75 residues), by SDS-PAGE followed by staining with Coomassie Blue R-250. The recombinant protein was made in *E. coli* BL21DE3 by using an IPTG-inducible plasmid, pet-11a, and purified as described in the section related to the examples. Lane 1: SDS-PAGE of soluble and insoluble fractions of non-IPTG induced cells. Lane 2: SDS-PAGE of soluble and insoluble fractions of cells induced with 0.5 mM IPTG. The HFt-MMP-PAS band is indicated by the black arrow and migrates at approximately 40 kDa, as opposed to a calculated mass of 28.5 kDa. This phenomenon is consistent with others reported for PASylated proteins and is due to a reduced SDS binding of PAS sequences. In addition, PAS sequences stain faintly with Coomassie Blue, which leads to the underestimation of the protein band in the gel.

The bacterial expression profile for HFt-MMP-PAS75 construct is shown in FIG. 4.

Example 3

Preparation of a PEGylated Version of the HFt Protein

Native HFt was PEGylated with PEG 5 kDa and used as a reference in size exclusion chromatography experiments (SEC). Solutions (2 mg/mL) were incubated with 1.0 mM methoxypolyethylene glycol maleimide 5 KDa (Sigma-Aldrich), in PBS at pH 7.0 and at room temperatures for about 2 hours with stirring. Subsequently, the samples were filtered and exchanged 5 times with $H_2O_{dd}$ using 30 kDa spin filtering devices from Amicon Ultra-15 (Millipore Corporate) to remove the excess reagents. The PEGylated sample (HFt-PEG5K) was sterile filtered and stored at 4° C.

Example 4

Assessment of the Hydrodynamic Volume for HFt, HFt-MMP-PAS40, HFt-MMP-PAS75 and HFt-PEG5K by Size Exclusion Chromatography (SEC)

SEC experiments were carried out by using a gel filtration Superose 6 column equilibrated with phosphate-buffered saline (PBS) at pH 7.5. All samples were prepared at 1 mg/mL in filtered PBS.

Figure 5:
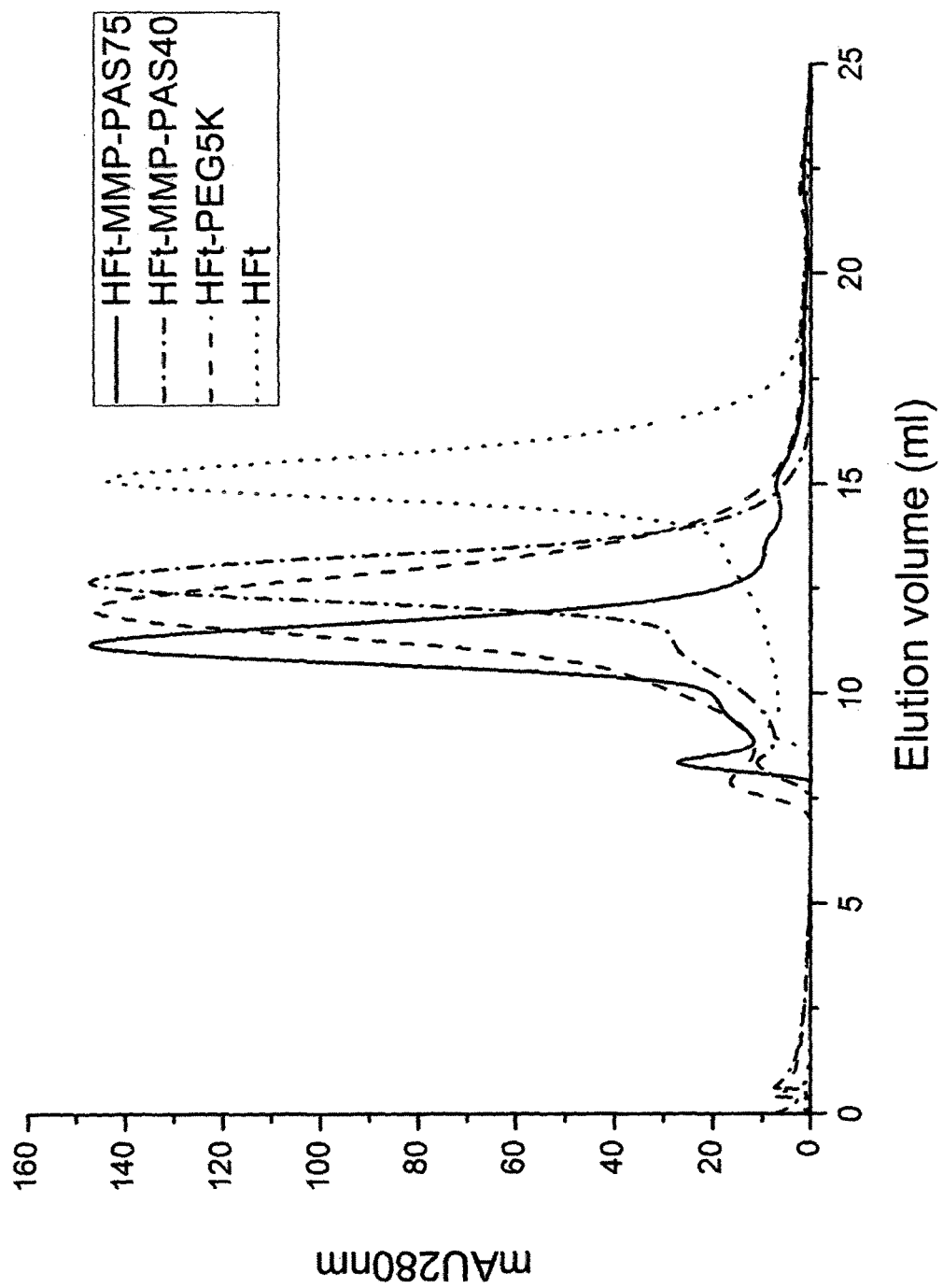
FIG. 5 shows the size exclusion chromatography profiles of native HFt (dotted lines) and of the fusion protein constructs HFt-MMP-PAS75 (solid lines), HFt-MMP-PAS40 (broken and dotted lines) or of HFt functionalized with polyethylene glycol (PEG) 5 kDa (HFt-PEG5K, broken lines).

All the SEC elution profiles were analyzed with Origin 8.0 (Originlab Corporation, Northampton, Mass.). The elution profiles for HFt and its fusion protein or functionalized versions are shown in FIG. 5. These results indicate that both of the PASylated versions have hydrodynamic volumes that are higher compared to the native protein and comparable with the PEGylated version (PEG 5 kDa) of HFt, with HFt-MMP-PAS75 slightly higher and HFt-MMP-PAS40 slightly lower. Furthermore, both of the PASylated versions have a more homogeneous and, monodisperse profile compared to the PEGylated version. These hydrodynamic volumes are considered as appropriate values for the purposes of the present inventors, and both of the HFt-MMP-PAS75 and HFt-MMP-PAS40 fusion proteins were further characterized and used for encapsulating the drugs and as nanocarriers for cancer treatment.

Example 5

Figure 6:
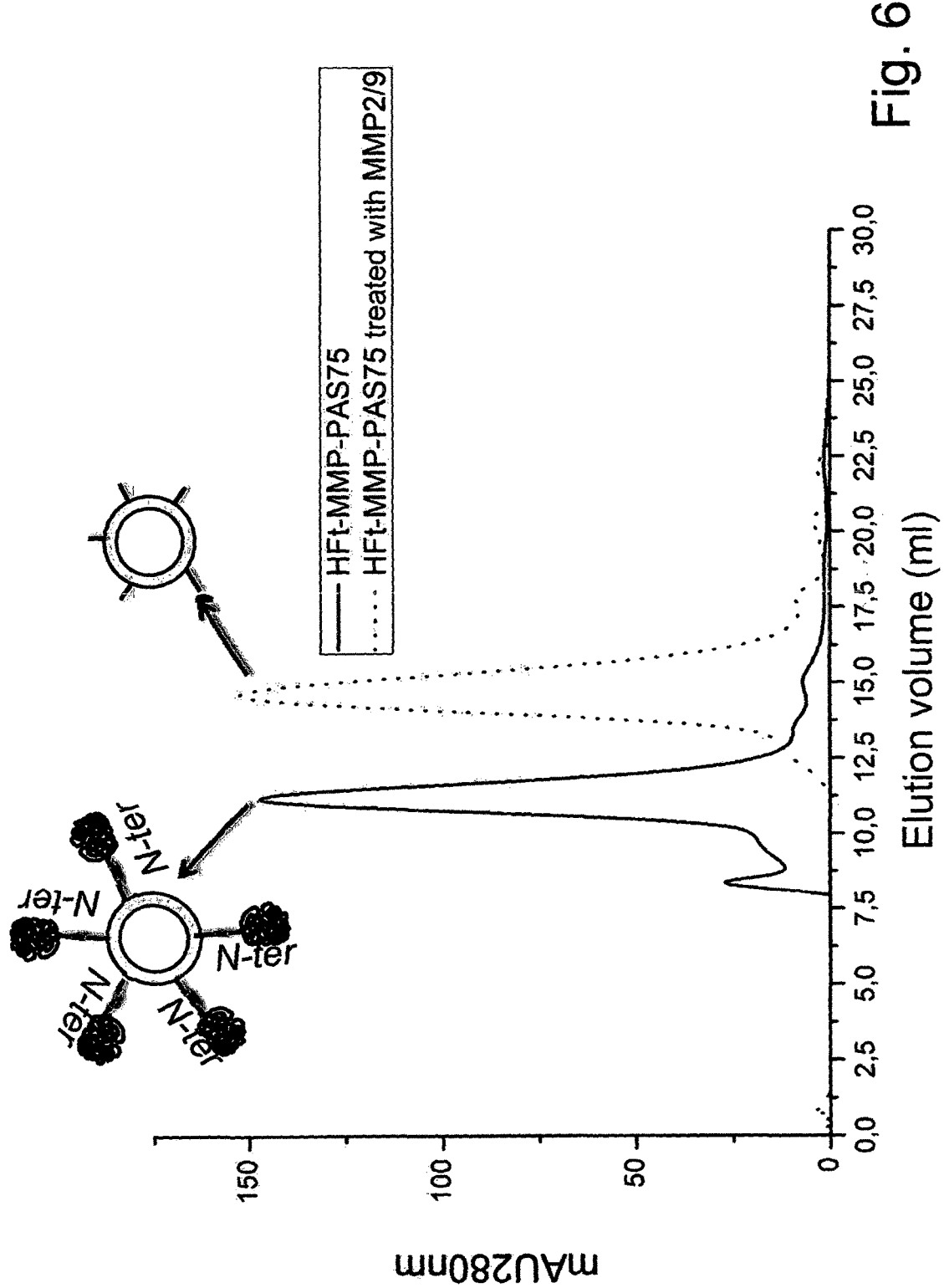
FIG. 6 shows the typical size exclusion chromatography profiles of HFt-MMP-PAS75, before (solid lines) and after (dotted lines) PAS removal by the proteases MMP-2/9 (Collagenase IV) in vitro.
Figure 7:
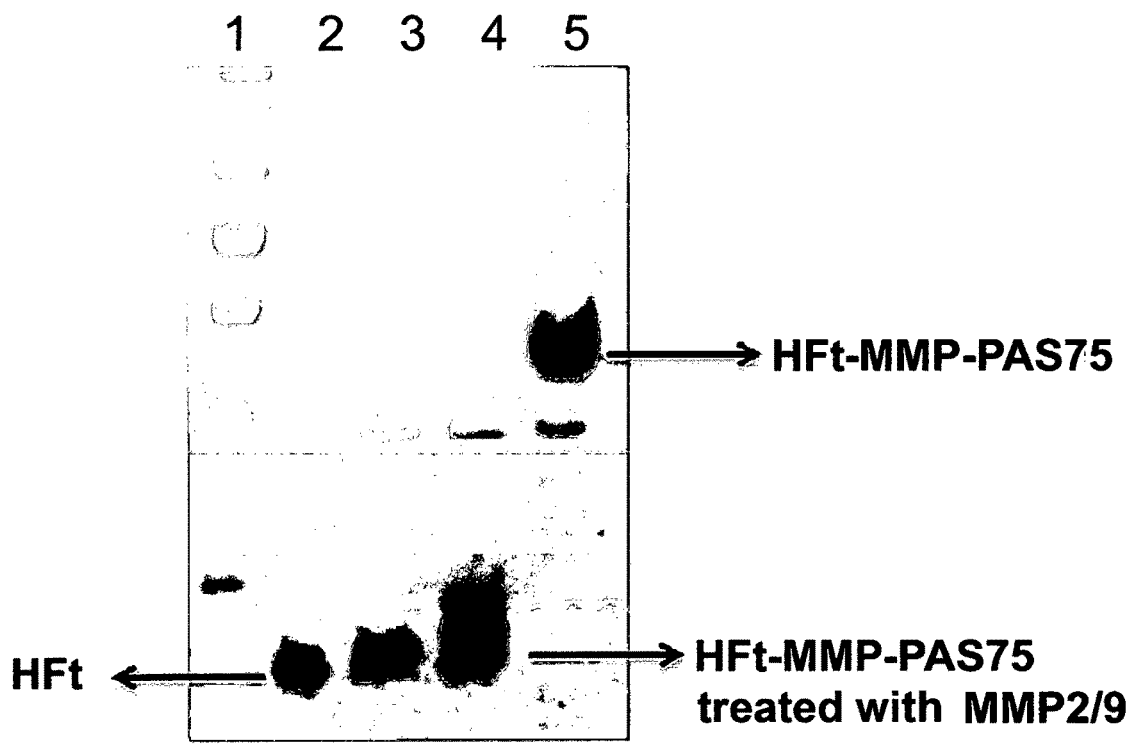
FIG. 7 shows the migration profiles of the HFt-MMP-PAS75 bands, before and after PAS removal by the proteases MMP-2/9 (Collagenase IV) in vitro. The SDS-PAGE was stained with Coomassie Blue R-250. Lane 1: protein marker; Lane 2: HFt (1 mg/ml); Lane 3: HFt-MMP-PAS75 (2 mg/ml) after in vitro digestion with 0.2 mg/ml MMP-2/9 proteases (collagenase IV); Lane 4: HFt-MMP-PAS75 (2 mg/ml) after in vitro digestion with 0.2 mg/ml MMP-2/9 proteases (collagenase IV).

Removal of the Protective PAS from HFt-MMP-PAS75 Fusion Protein in the Presence of Proteases MMP2/9 In Vitro In order to analyze the enzymatic cleavage of MMP-sensitive conjugates, the cleavage of HFt-MMP-PAS75 was studied in the presence of MMP-2/9. A solution of HFt-MMP-PAS75 was mixed with collagenase IV (containing MMP2 and 9) and incubated at 37° C. for 2 hours. Then, the samples were tested in SEC experiments using a gel filtration Superose 6 column equilibrated with phosphate-buffered saline (PBS) at pH 7.5 (FIG. 6) and by SDS gel chromatography (FIG. 7).

Example 6

Preparation of HFt-MMP-PAS40 and HFt-MMP-PAS75 Carrying a Chemotherapeutic Agent As the chemotherapeutic agent, the inventors reported an example in which the drug doxorubicin (DOXO) was used. DOXO was encapsulated within the protein cavity of the two fusion proteins by exploiting the protein uncoupling-coupling process as a function of the pH. The reaction was performed by using a preferred concentration of 1.5 mM DOXO and a preferred concentration of 5 µM protein. The encapsulating reaction was carried out by gently mixing DOXO and the protein in the dark under acidic conditions at a pH comprised between 1.8 and 2.5, more preferably at 2.0. The reaction temperature is usually comprised between +10° C. and +40° C., preferably +25° C., for a period of time from 5 to 30 minutes, preferably for 10 minutes. Subsequently, the solution was rapidly adjusted at a pH comprised between 6.5 and 9.0, more preferably at pH 7.5, using concentrated NaOH and left stirring for an additional 30 minutes. Then, the solution was centrifuged at 15,000 rpm for 30 minutes at 4° C. and the supernatant was dialysed in pH 7.4 phosphate-buffered saline (PBS) for a period comprised between 10 and 16 hours, in the dark at 4° C. As the final step, the solution was adjusted at the desired concentration with 30 kDa spin devices Amicon Ultra-15 (Millipore Corporate). The HFt nanoparticles (NPs) containing DOXO (HFt-MMP-PAS40-DOXO and HFt-MMP-PAS75-DOXO) were sterile filtered and stored at 4° C. in the dark.

Example 7

Testing of the Encapsulating Yields of the Drug Doxorubicin

The ability of encapsulating doxorubicin by two of the established constructs (HFt-MMP-PAS40 and HFt-MMP-PAS75) was tested and compared with that of the native HFt protein and with other data from the literature. The amount of doxorubicin was determined after the samples had been incubated with acidic isopropanol (2N HCl) at 25° C. for a period of 30 minutes. The assessment occurred by using a UV-visible spectrophotometer with readings at 485 nm and an extinction coefficient for DOXO of 9250 $M^{-1}$ $cm^{-1}$.

The relative yields were then reported in terms of % protein recovery and number of doxorubicin molecules encapsulated (FIG. 8). It can be seen that the constructs subject matter of this patent surprisingly and unexpectedly have acquired a better ability of encapsulating the drug doxorubicin by at least a factor of 6 compared to native HFt.

Example 8

Testing of the Stability of the Ferritin-Doxorubicin Complexes

Figure 9:
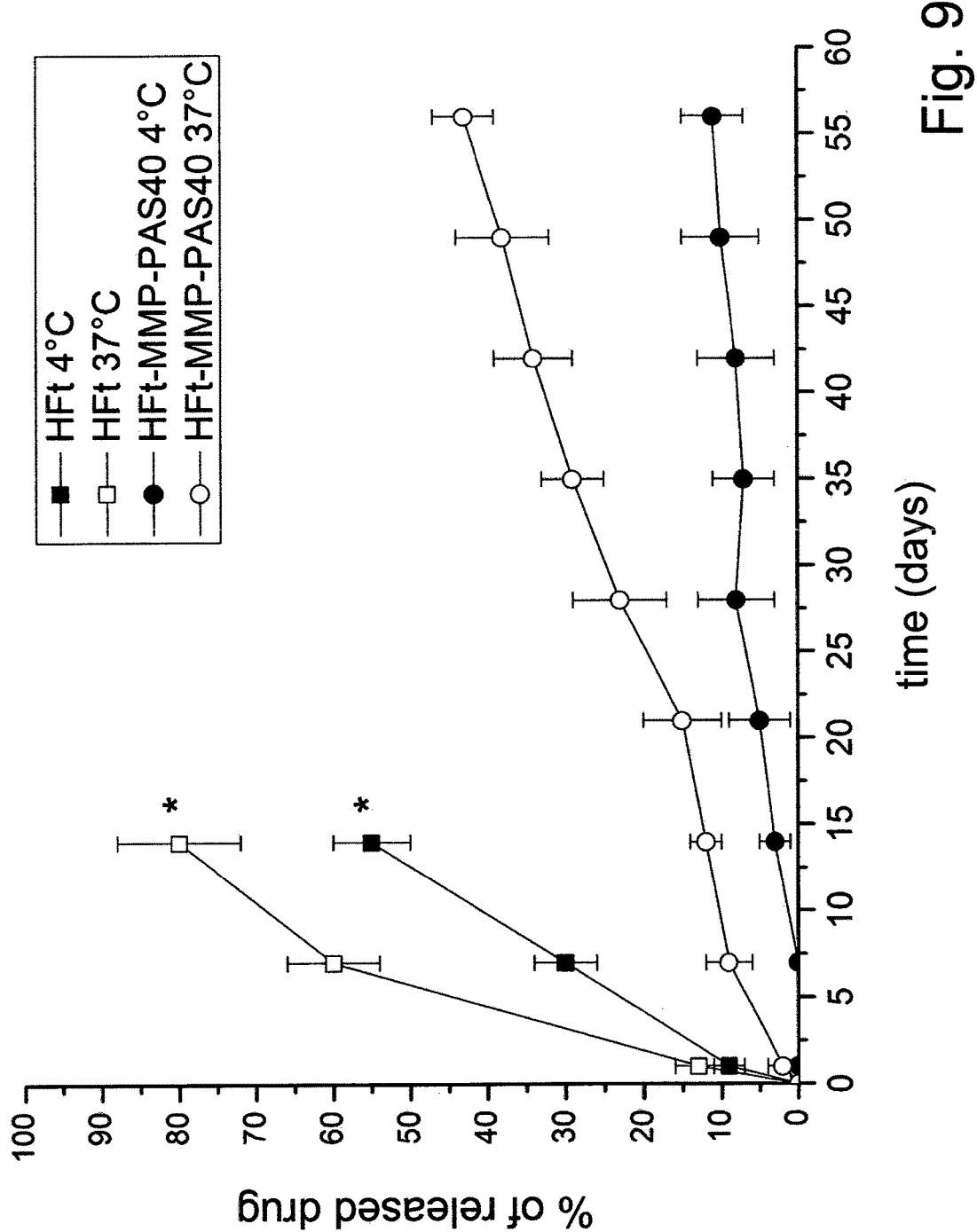
FIG. 9 shows a typical size exclusion chromatography profile of HFt-MMP-PAS40-DOXO with readings at 280 nm (solid lines) and 485 nm (dotted lines).

The stability of the ferritin-Doxorubicin complexes was tested at 4° C. and 37° C. in terms of % drug release over time. The % of doxorubicin released was assessed by size exclusion chromatography (SEC) by using a gel filtration Superose 6 column equilibrated with phosphate-buffered saline (PBS) at pH 7.5. All samples were prepared at 1 mg/mL in filtered PBS, following the absorbance at 280 and 485 nm. A typical elution profile for HFt-MMP-PAS40-DOXO is shown in FIG. 9.

Figure 10:
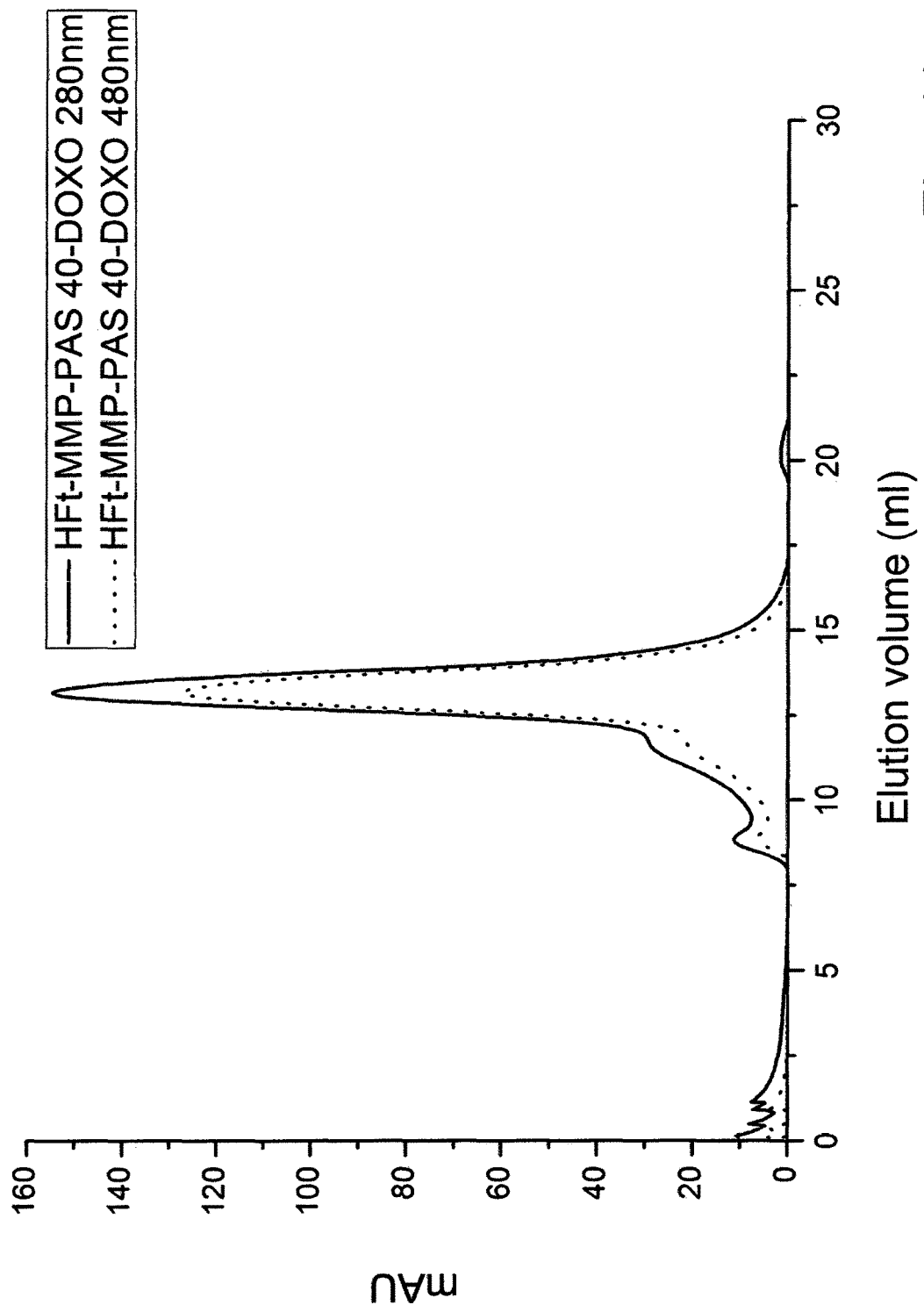
FIG. 10 shows the stability of the ferritin-Doxorubicin complexes (HFt-DOXO, HFt-MMP-PAS40-DOXO and HFt-MMP-PAS75-DOXO) at 4° C. and 37° C. in terms of % drug release over time. Owing to the modifications carried out on HFt described in this patent, the HFt-MMP-PAS40 construct (the same results were also obtained with HFt-MMP-PAS75) is far more stable (lower % of drug released over time when stored at 4 or 37° C.) in its drug-bound form compared to the corresponding native HFt construct. The asterisk (*) indicates that the amount of drug released could not be determined beyond this period of time in native HFt samples, as the material tended to become cloudy and precipitate.

As shown in FIG. 10, owing to the modifications carried out on HFt described in this patent, the HFt-MMP-PAS40 construct (the same results were also obtained with HFt-MMP-PAS75) is far more stable in its drug-bound form compared to the corresponding native HFt construct.

Example 9

Anti-Proliferative Effects of HFt-MMP-PAS75-DOXO In Vitro

In order to test the proliferation, human sarcoma cells (HT-1080) were plated on 96-well plates at approximately $5 \times 10^3$/well in 200 µl of complete medium at 37° C. The following day, the wells received PBS, HFt-MMP-PAS75, Doxorubicin or HFt-MMP-PAS75-DOXO, in triplicate, at different concentrations in doxorubicin, and the cells were cultured for 72 hours. During the last 4 hours in culture, [$^3$H]-thymidine was added (1 µCi/well; 1 mCi=37 MBq), and the incorporation was assessed by lysing the washed cells and counting the TCA-precipitable radioactivity.

Figure 11:
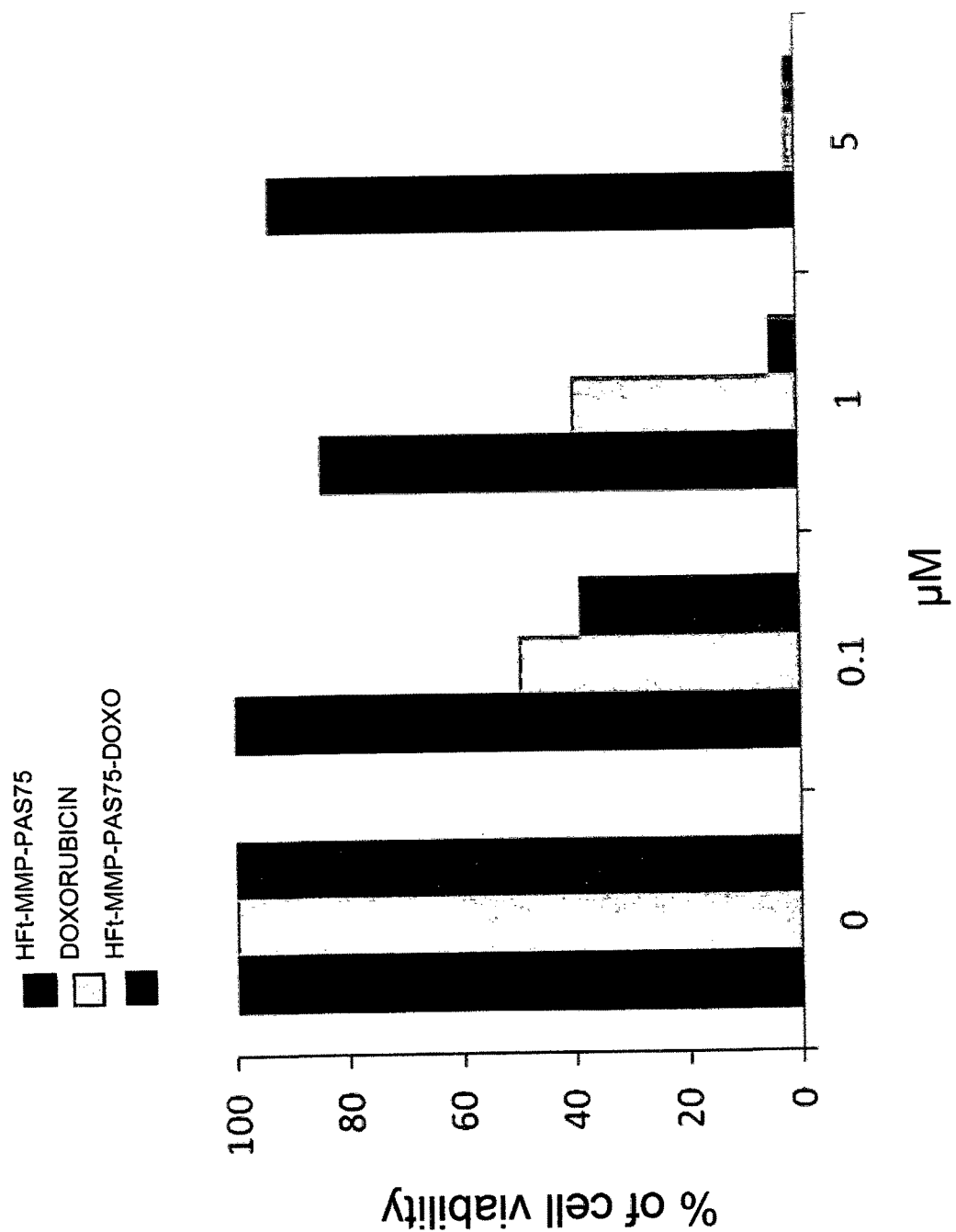
FIG. 11 shows the anti-proliferative activity of DOXO-RUBICIN, HFt-MMP-PAS75 and HFt-MMP-PAS75-DOXO against sarcoma HT-1080 cells.

The anti-proliferative effects of HFt-MMP-PAS75-DOXO for the cultured cancer cells are shown in FIG. 11. The results indicate that HFt-MMP-PAS75-DOXO effectively inhibits sarcoma cells grown in vitro in a concentration-dependent way, with $IC_{50}$ values identical or even lower compared to nude doxorubicin. These results are of major importance in the light of the potential therapeutic applications.

Example 10

Pharmacokinetic Experiments on Doxorubicin-Containing Compounds

Figure 12:
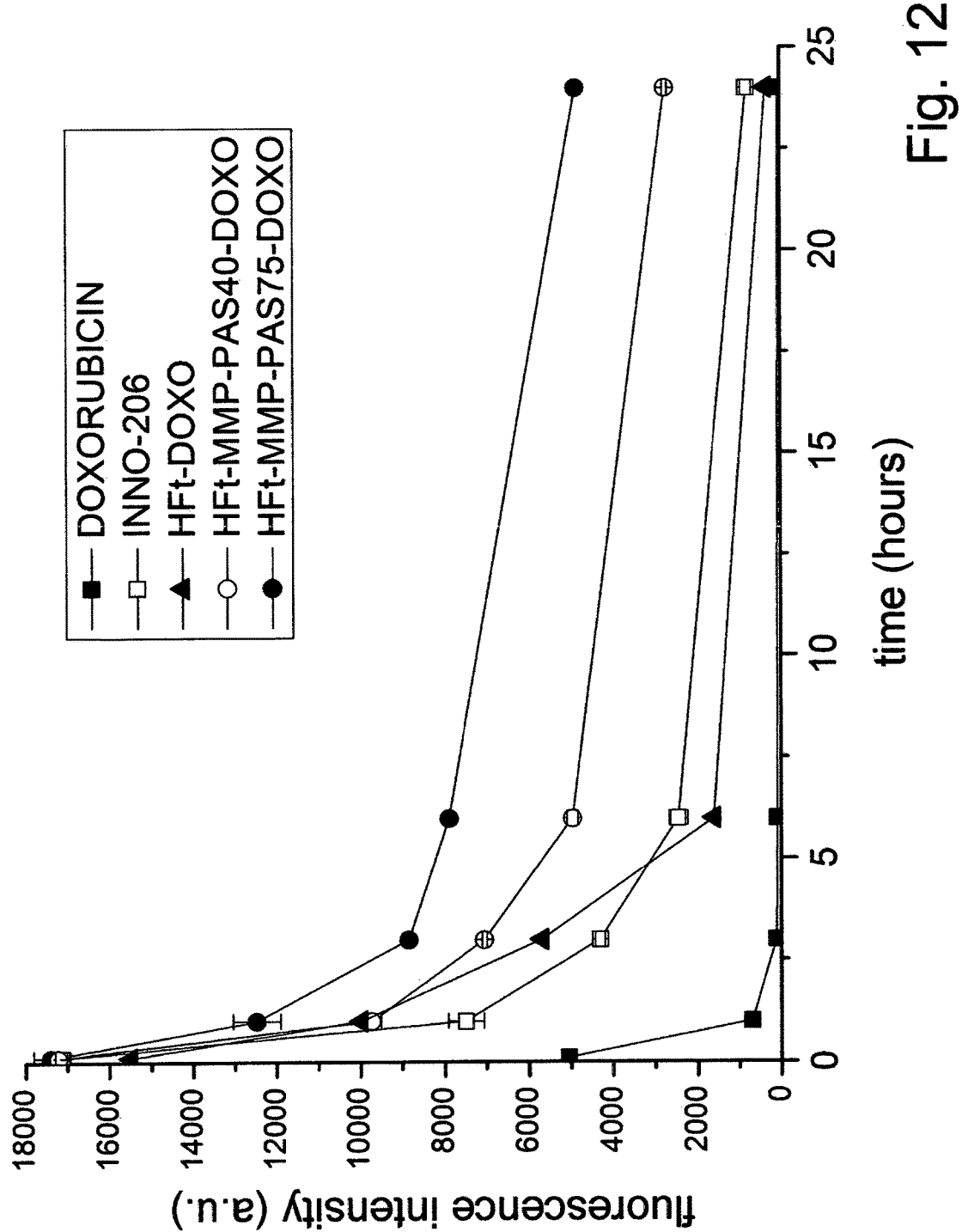
FIG. 12 shows the results from pharmacokinetic experiments on doxorubicin-containing compounds. Doxorubicin plasma concentrations were calculated at different times (10, 60, 180, 360 and 1440 minutes) after intravenous injections in healthy mice of the naked drugs doxorubicin and INNO-206 (a new and more active doxorubicin formulation) or of doxorubicin encapsulated in the ferritin-based compounds: native HFt, HFt-MMP-PAS40 and HFt-MMP-PAS75.

In order to assess the plasma stability and the pharmacokinetics, the doxorubicin-containing compounds were injected intravenously in healthy mice. Then, blood samples were drawn at different times (10, 60, 180, 360 and 1440 minutes), diluted 1:10 with acidic isopropanol (0.75 N HCl) and frozen at −20° C. The following day, the extracted doxorubicin was quantified by measuring the fluorescence at an excitation of 485 nm and an emission of 590 nm, using a multimode scanning plate reader. The following samples were assessed: doxorubicin, INNO-206 (a new and more active doxorubicin formulation), HFt-DOXO, HFt-MMP-PAS40-DOXO and HFt-MMP-PAS75-DOXO. The results are shown in FIG. 12.

Example 11

Figure 13:
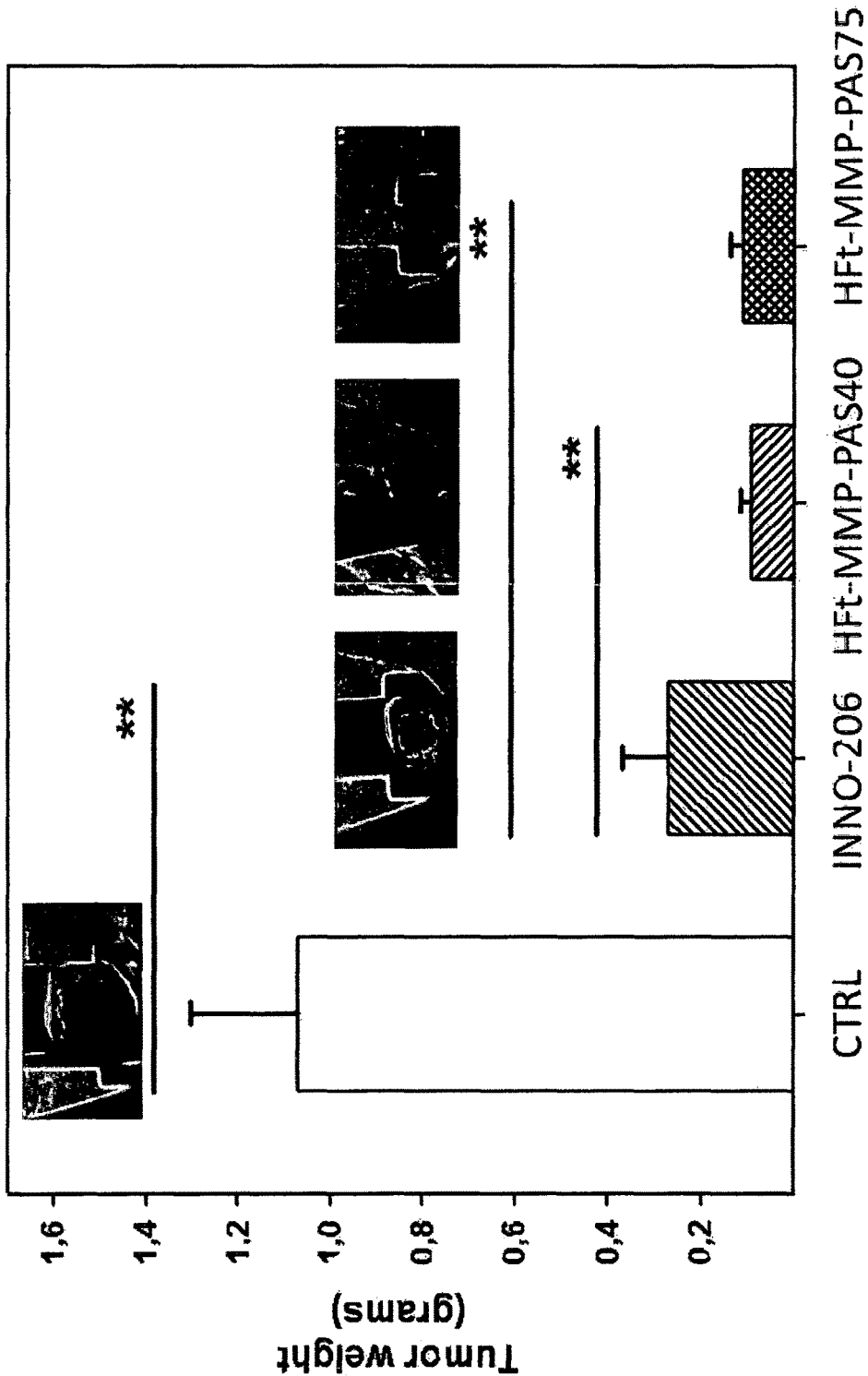
FIG. 13 shows a typical experiment for assessing the therapeutic effect in mice bearing a human pancreatic tumour (Xenografts). Mice groups (n=6), once the tumour sizes reached approximately 100 mm³, were treated 4 times (every 4 days) with one dose of 5 mg/kg doxorubicin. The compounds tested were: INNO-206, HFt-MMP-PAS40-DOXO and HFt-MMP-PAS75-DOXO. In the figure, the weight of the tumour (and of the representative images) is reported after about 3 weeks from the beginning of treatment.

Assessment of the Therapeutic Effect of doxorubicin-Containing Compounds in Animal Models A typical experiment for assessing the therapeutic effect of doxorubicin-containing compounds was carried out in mice bearing a human pancreatic tumour (Xenografts). Mice groups (n=6), once the tumour sizes reached approximately 100 mm$^3$, were treated 4 times (every 4 days) with one dose of 5 mg/kg doxorubicin. The compounds tested were: INNO-206, HFt-MMP-PAS40-DOXO and HFt-MMP-PAS75-DOXO. The result of a typical experiment for the tumour weight (and representative images) after about 3 weeks from the beginning of treatment is reported in FIG. 13. As shown in the figure, the doxorubicin-containing constructs established by the present inventors have a higher therapeutic activity compared to the new formulation of the drug doxorubicin (INNO-206) at the doses tested.

The invention claimed is:

1. A fusion protein comprising at least three domains, wherein:
   (a) a first domain comprising a polypeptide having an amino acid sequence at least 90% identical to the heavy chain of native human ferritin;
   (b) a second domain comprising a polypeptide having the amino acid sequence of a matrix metalloproteinase (MMP) cleavage site; and
   (c) a third domain comprising a polypeptide consisting essentially of proline, serine and alanine (PAS) residues;
   wherein the third domain fusion protein is at least 20 and less than 80 amino acid residues in length; and
   wherein the fusion protein is in a linear arrangement of amino-terminus to carboxy-terminus of the first domain, the second domain, and the third domain.

2. The fusion protein according to claim 1, wherein the first domain comprises the amino acid sequence of SEQ ID NO: 1 or SEQ ID NO: 2.

3. The fusion protein according to claim 1, wherein the second domain comprises the amino acid sequence of a matrix metalloproteinase (MMP) cleavage site selected from the group consisting of MMP-2, MMP-3, MMP-7 and MMP-9.

4. The fusion protein according to claim 3, wherein the amino acid sequence of the matrixmetalloproteinase (MMP) cleavage site is selected from the group consisting of SEQ ID NOs: 3-8.

5. The fusion protein according to claim 1, wherein the proline residues of the PAS polypeptide amount to 10-40% of the total amino acid residues of the PAS polypeptide.

6. The fusion protein according to claim 1, wherein the amino acid sequence of the PAS polypeptide is selected from SEQ ID NO:9 and SEQ ID NO:10.

7. The fusion protein according to claim 1, comprising a first and/or second linker amino acid sequence(s) respectively linking the first domain to the second domain and/or the second domain to the third domain.

8. The fusion protein according to claim 1, which is linked to an active ingredient and/or imaging agent.

9. The fusion protein of claim 1, wherein the first domain comprises a polypeptide having the amino acid sequence of the heavy chain of native human ferritin.

10. The fusion protein according to claim 2, wherein the PAS is between 20 and 80 amino acid residues in length.

11. The fusion protein according to claim 2, wherein the PAS is between 40 and 75 amino acid residues in length.

12. The fusion protein according to claim 7, wherein the first and the second linker sequences are the same.

13. The fusion protein according to claim 7, wherein the first and the second linker amino acid sequences are different from one another.

\* \* \* \* \*